United States Patent [19]
Archibald

[11] 4,126,137
[45] Nov. 21, 1978

[54] ELECTROSURGICAL UNIT

[75] Inventor: G. Kent Archibald, White Bear Lake, Minn.

[73] Assignee: Minnesota Mining and Manufacturing Company, Saint Paul, Minn.

[21] Appl. No.: 760,847

[22] Filed: Jan. 21, 1977

[51] Int. Cl.² ................ A61B 17/36; A61N 3/00
[52] U.S. Cl. ................ 128/303.14; 128/303.17; 128/422
[58] Field of Search ............ 128/303.14, 303.17, 128/303.13, 419 D, 422

[56] References Cited

U.S. PATENT DOCUMENTS

| | | | |
|---|---|---|---|
| 3,127,895 | 4/1964 | Kendall et al. | 128/422 |
| 3,523,539 | 8/1970 | Lavezzo et al. | 128/422 |
| 3,601,126 | 8/1971 | Estes | 128/303.14 |
| 3,791,373 | 2/1974 | Winkler et al. | 128/422 X |
| 3,886,950 | 6/1975 | Ukkestad | 128/419 D |
| 3,923,063 | 12/1975 | Andrews et al. | 128/303.14 |
| 3,964,487 | 6/1976 | Judson | 128/303.14 |
| 4,057,063 | 11/1977 | Gieles et al. | 128/303.17 |

FOREIGN PATENT DOCUMENTS 2,306,668  11/1976  France ................ 128/303.17

Primary Examiner—Lee S. Cohen
Attorney, Agent, or Firm—Cruzan Alexander; Donald M. Sell; Robert L. Marben

[57] ABSTRACT

An electrosurgical unit having a feedback control circuit for providing control of the power amplifier of the unit so power delivered to tissue presented between the active and return electrodes of the unit will be substantially constant over the range of impedance presented by various tissues that are encountered. The feedback signal to the power amplifier is determined from a comparison of a power level reference signal and the mathematical product of two signals which are derived from a sensed current in the unit that is directly related to current delivered to tissue and a sensed voltage that is directly related to voltage delivered to tissue. A non-linear compensation circuit is also disclosed for use in the feedback circuit.

6 Claims, 4 Drawing Figures

ELECTROSURGICAL UNIT

BACKGROUND OF THE INVENTION

1. Field of the Invention

The invention presented herein relates to electrosurgical units and, more specifically, to circuitry for providing automatic control of the output power at a selected level over the usual impedance range of electrically conductive tissue encountered when using such units.

2. Description of the Prior Art

A wide variety of electrosurgical units for generating various high frequency output waveforms for electrosurgical procedures are known in the art. A selected waveform output from an electrosurgical unit is applied to a patient by the use of an active electrode placed in contact with the patient at the point where a desired surgical procedure is to be carried out on tissue with current return provided via the patient and a plate or return electrode positioned in electrical contact with the patient. The active electrode provides a small area contact with the tissue of the patient to cause the current density at such contact to be high enough to generate heat sufficient to accomplish the desired surgical procedure.

Since the impedance of the current path is a function of the different electrically conductive tissue types that may be encountered, the power delivered by the electrosurgical unit will vary dependent on the tissue encountered when the unit is set to provide a selected desired output. It has been a common practice to merely match the output impedance of the electrosurgical unit to the median of the expected impedance range of the tissue. This method is not acceptable since the output power decreases as the impedance varies from the median or center designed value. In order that adequate power be provided at both low or high impedance tissue with such method, it is necessary to provide for a power level at the median of the impedance range which may be excessive resulting in unnecessary tissue damage.

U.S. Pat. No. 3,601,126 points out the power level problem involved due to the range of impedance that is encountered when using an electrosurgical unit. The patent purports to solve this problem by monitoring the load current from the secondary of an output transformer by the use of a square law detector, the output of which is compared with a reference voltage level with the difference that is detected being used to vary the output of the electrosurgical unit. Such an arrangement, while providing a constant load current, produces in a linear increase in power to the load as the load impedance increases rather than providing a constant power output. Further, by sensing current flow on the secondary side of the output transformer, a degradation of high frequency isolation is presented.

SUMMARY OF THE INVENTION

This invention provides an improved electrosurgical unit for providing electrosurgical currents to tissue from a controllable power amplifier coupled via an output transformer to an active electrode and return electrode, the improvement residing in a negative feedback control circuit which includes a first sensing means for sensing a current that is directly related to the current delivered to tissue presented between the active and return electrodes of the unit; a second sensing means for sensing a voltage that is directly related to the voltage presented across the tissue presented between the active and return electrodes of the unit with a function generator connected to the first and second sensing means for obtaining two signals from the sensings made by the first and second sensing means and providing a signal that is directly related to the mathematical product of the two signals which is applied to a comparator-amplifier circuit in the feedback circuit where it is compared to a power level reference signal, the magnitude of which is selected by the operator. The output of the comparator-amplifier is connected to the controllable power amplifier of the electrosurgical unit whereby a transfer of a constant power level in accordance with the selected power level reference signal is made to tissue when presented between the active and return electrodes of the electrosurgical unit.

Should the power output not be as constant as desired, due possibly to non-linearities introduced by various components selected for the circuit just described, another embodiment of the invention provides for a non-linear compensation circuit to correct for such problem. The compensation circuit is provided in the feedback circuit as a part of the function generator connected to the first and second sensing means. A suitable compensation circuit may be used that is responsive to a signal connected to a first input with another signal connected to a second input for providing an output signal from the compensation circuit that is a modification of the signal applied to the one input with the modification being dependent on the magnitude of the signal provided to the second input. The output signal of the compensation circuit is reduced as the signal to the second input increases. Accordingly, if any non-linearity that may be introduced shows a need to increase the power at the high end portion of the impedance range, the signal from the first sensing circuit, which is indicative of the current delivered to the tissue, is applied to the first input of the compensation circuit, while the signal from the second sensing circuit, which is indicative of the voltage presented across the tissue, is applied to the second input. This arrangement will also cause some increase in power at the low end power of the impedance range, but a greater increase will be introduced at the high end of the impedance range. Similarly, if any non-linearity that may be introduced shows a need to increase the power at the low end portion of the impedance range, the signal from the second sensing circuit, which is indicative of the voltage presented across the tissue, is applied to the first input, while the signal from the first sensing circuit, which is indicative of the current delivered to the tissue, is applied to the second input. This introduces an increase in power at the low end portion of the impedance range that is greater than any increase introduced at the high end portion of the impedance range. In each case, the output signal from the compensation circuit and the signal connected to the second input are the two signals from which the function generator provides a signal that is directly related to the mathematical product of the two signals.

DETAILED DESCRIPTION

Figure 1:
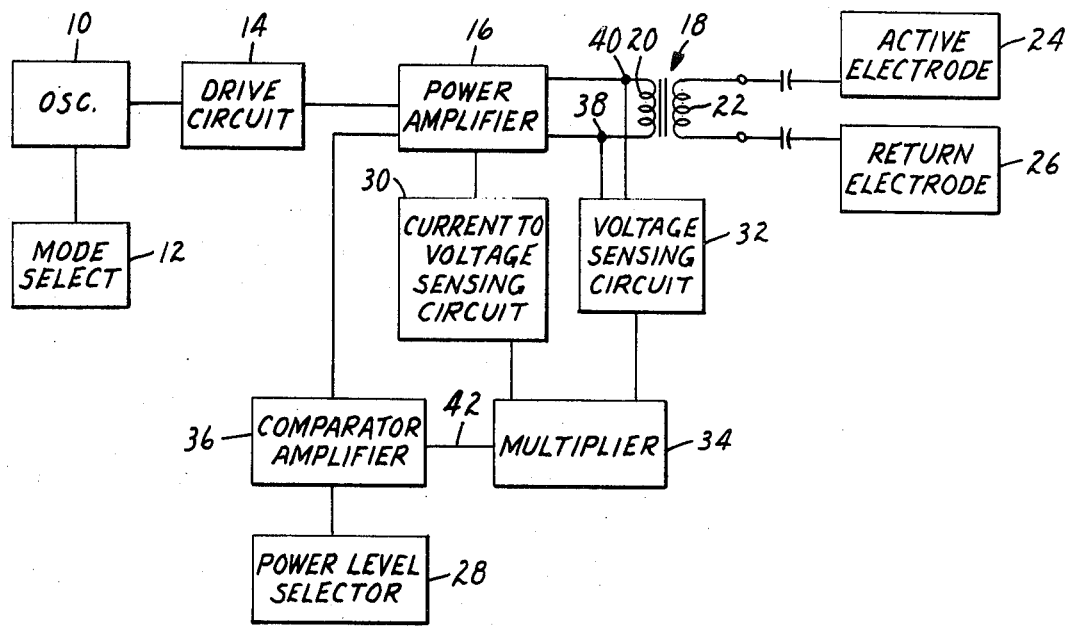
FIG. 1 is a block diagram of electronic circuitry forming a preferred embodiment of the electrosurgical unit of the present invention.

Referring to FIG. 1 of the drawing, the electronic circuitry shown in block diagram form consisting of the oscillator 10, the mode select 12, drive circuit 14, controllable power amplifier 16, output transformer 18 having a primary winding 20 and a secondary winding 22, an active electrode 24 capacitively coupled to one end of the secondary winding 22 and a return or patient electrode 26 capacitively coupled to the other end of the secondary winding 22 is representative of circuitry found in a number of known electrosurgical units for providing electrosurgical currents to tissue presented between the active and return electrodes. A power level selector 28 is also shown which generally, in known units, is connected directly to a power control in the power amplifier 16.

The oscillator 10 is designed to generate electrosurgical currents, such as cutting and coagulation currents, with the mode select 12 providing the means operated by the operator to select the desired type of electrosurgical current. The selected output from oscillator 10 is applied to the drive circuit 14 which serves to amplify the output received from the oscillator with the controllable power amplifier 16 serving to further amplify the desired electrosurgical current in accordance with a signal from the power level selector 28 as selected by the operator to obtain a desired power level for the selected current. The output transformer 18 is used to couple the output of the power amplifier 16 to the tissue of the patient which is connected between the active electrode 24 and the return or patient electrode 26.

It is known that the arrangement of FIG. 1 described to this point will not deliver power at a substantially constant level over the range of impedance of the various types of tissue that may be presented to the active and return electrodes of the unit. The remaining portion of the circuitry shown in FIG. 1, which includes a first sensing means provided by the current to voltage sensing circuit 30, a second sensing means provided by the voltage sensing circuit 32, a function generator provided by the multiplier 34 and comparator-amplifier 36 to which the power level selector 28 is connected, provides a negative feedback circuit which is effective to control the power amplifier 16 to adjust the power level delivered to the tissue when presented between the active electrode 24 and return electrode 26 so it is substantially constant over the range of impedance usually presented by the various types of tissue encountered during various surgical procedures that may be carried out when using the electrosurgical unit.

The first sensing means provided by the current to voltage sensing circuit 30 provides an electrical signal to the multiplier 34 that is directly related to the current flow to the primary winding 20 and, therefore, directly related to the current delivered to tissue when presented to the active and return electrodes.

The second sensing means provided by the voltage sensing circuit 32 is connected at points 38 and 40 of the primary winding 20 to provide a voltage signal to the multiplier 34 that is directly related to the voltage across the primary winding 20 and, therefore, directly related to the voltage provided across the tissue when presented to the active and return electrodes. The multiplier 34 provides an output voltage signal on conductor 42 that is applied to the comparator-amplifier 36 which is proportional to the mathematical product of the signals from the sensing circuits 30 and 32 and, therefore, proportional to the power transferred to the load circuit by the primary winding 20. A voltage reference signal is provided to the comparator-amplifier 36 from the power selector 28, which is set by the operator for a desired power level at the active and passive electrodes 24 and 26, respectively. If a difference exists between the voltage signal from the multiplier 34 and the voltage reference signal from the power level selector 28, such difference is applied to the power control in the controllable power amplifier 16 to change the current flow in the primary winding 20 so the difference detected is reduced to approximately zero.

Figure 2:
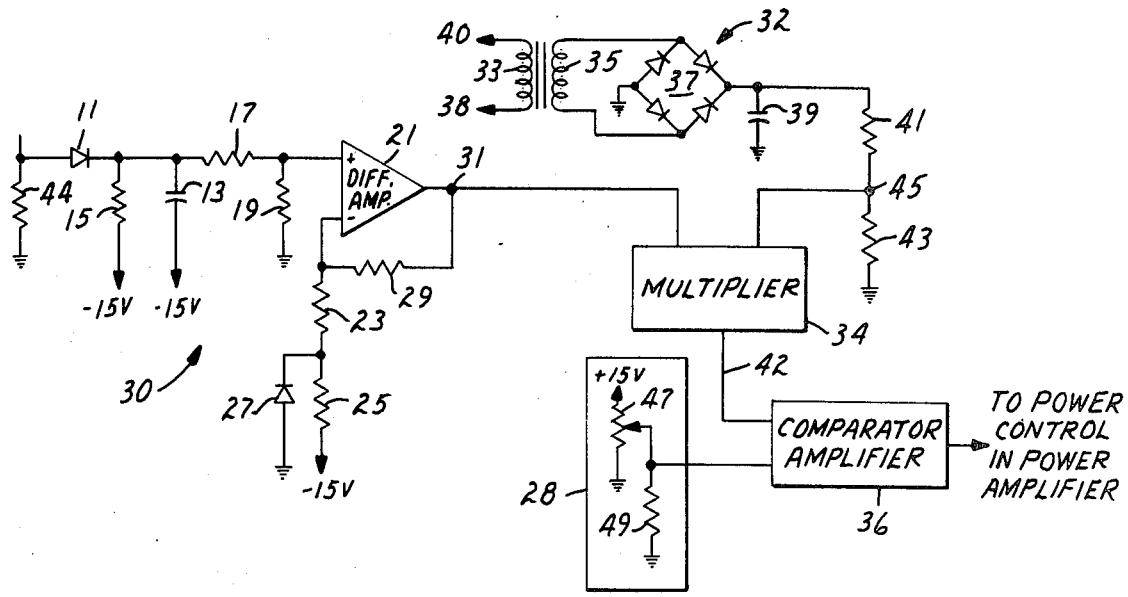
FIG. 2 is a schematic and block diagram showing of a portion of the block diagram of FIG. 1.

FIG. 2 is a schematic and block diagram showing of the negative feedback circuit that has been described in connection with FIG. 1, with details provided with respect to suitable circuits usable as the voltage sensing circuit 32, the current to voltage sensing circuit 30 and the power level selector 28. The multiplier 34, which is the function generator needed for the circuit of FIG. 1, is not shown in detail since it may, for example, be provided by a standard commercially available multiplier circuit available as type AD533 from Analog Devices, Inc., Norwood, Mass.

The comparator-amplifier 36 can be provided by a differential amplifier connected as a comparator with the output of the comparator appropriately amplified to provide the necessary drive signal to the power control portion of the power amplifier 16.

An exemplary current to voltage sensing circuit 30 is shown connected for sensing the current through a resistor 44. The resistor 44 is provided in the power amplifier 16 and is selected as a resistor that carries all or a known proportional part of the current that flows through the primary winding 20, so the circuit 30 will provide a voltage signal that is directly related to the current flow in the primary winding 20 and in the secondary winding 22. The voltage appearing across the resistor 44 causes current to flow to a holding circuit portion which includes the diode 11, capacitor 13 and a discharge resistor 15 for the capacitor 13. The voltage at the capacitor 13 is applied to the two series connected resistors 17 and 19 which connect between one side of the capacitor 13 and ground. The voltage appearing across resistor 19 is applied to the positive input terminal of a differential amplifier 21 which has two series connected resistors 23 and 25 connected between the negative input of the amplifier 21 and a negative voltage. A diode 27 is connected between ground and the connection common to resistors 23 and 25 and serves to compensate for the voltage drop that occurs across diode 11. A resistor 29 is connected between the output 31 of the amplifier 21 and its negative input terminal. Therefore, the differential amplifier circuit as described, amplifies the difference between the voltage at the cathodes of diodes 11 and 27. The output 31 of the amplifier 21 is connected to the multiplier 34.

An exemplary circuit for the voltage sensing circuit 32 includes a sensing transformer that has its primary 33 connected across the primary 20 of the output transformer 18. A sensing transformer of the step-down type is suitable. The output of the secondary 35 of the sensing transformer is connected to a full-wave rectifier 37, the output of which is connected across a capacitor 39. Two series connected resistors 41 and 43 connect across the capacitor 39 with the connection 45 common connected to the multiplier 34 to provide it with a voltage signal that is directly related to the voltage presented across the primary winding 20 and, therefore, directly related to the voltage between active electrode 24 and return electrode 26.

An exemplary circuit for the power level selector 28 is shown in FIG. 2. It includes a potentiometer 47 connected between a voltage source and ground with the adjustable connection of the potentiometer connected to ground via a resistor 49 and to the comparator-amplifier 36 to provide the reference input signal to the comparator-amplifier 36.

Figure 3:
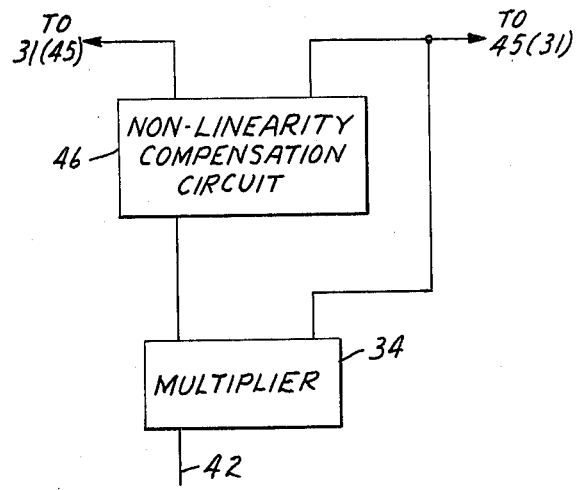
FIG. 3 is a block diagram showing a modification of a portion of the block diagram of FIG. 1.

While a selection of the various components for the circuits described is not considered critical, situations may arise wherein non-linearities are introduced by the various circuit components that have been selected to cause the power output level not to be as constant as desired. The non-linearity that is introduced may be compensated by the use of a non-linearity compensation circuit in the feedback circuit. FIG. 3 shows how such a compensation circuit 46 is connected in the circuitry of FIG. 2 to provide the needed compensation. The compensation circuit 46 and the multiplier 34 are viewed as providing a function generator.

Figure 4:
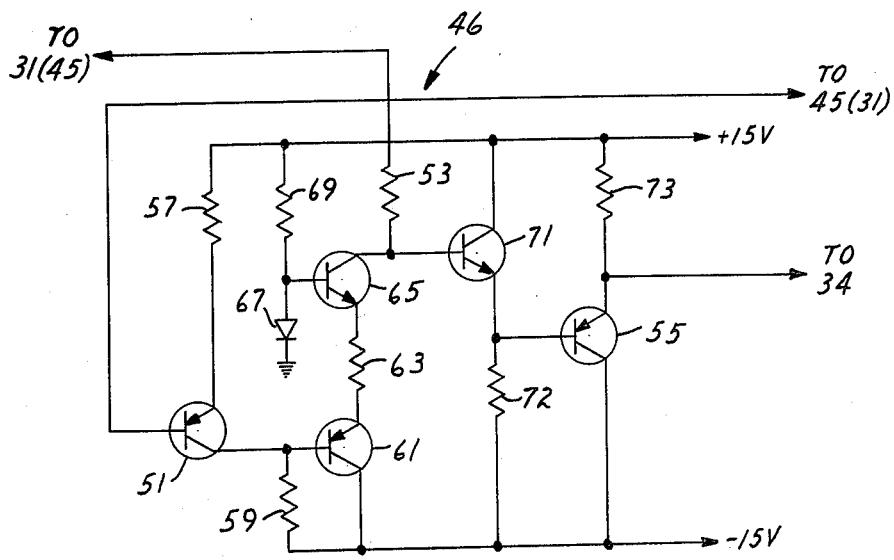
FIG. 4 is a schematic of a portion of the block diagram of FIG. 3.

An exemplary circuit for use as a non-linearity compensation circuit 46, as indicated in FIG. 3, is shown in detail in FIG. 4. If the circuitry per FIG. 1, i.e., without the compensation circuit 46, indicates there is need for compensation to raise the power level at the high impedance end portion of the impedance range, the resistor 53, which provides a first input for the circuitry 46 is connected to the output 31 of the current to voltage sensing circuit 30. The base electrode of transistor 51, which provides a second input for the circuitry 46, is connected to the connection 45 of the voltage sensing circuit 32, which is also connected to the multiplier 34 to provide one input to the multiplier 34. If there is a need for compensation to raise the power level at the low end portion rather than at the high end portion of the impedance range, the output 31 of the current to voltage sensing circuit 30 is connected to the second input (transistor 51) for the compensation circuitry 46 and to one input of the multiplier 34 with the voltage sensing circuit having the point 45 connected to the first input of the compensation circuit 46 provided at the resistor 53. In each of the two situations mentioned, the second input to the multiplier 34 is obtained from the emitter of the transistor 55. In the case of the block diagram showing in FIG. 3, the two possible connections are indicated by using reference numerals 31 and 45 for one situation with reference numerals (31) and (45) used for the second situation.

In addition to the components mentioned, the compensation circuit of FIG. 4 includes a resistor 57 connected between the emitter of transistor 51 and a positive voltage source with a resistor 59 provided between the collector of transistor 51 and a negative voltage source. The resistors 57 and 59 are of the same magnitude and the positive and negative voltage sources are of the same magnitude, so the transistor 51, which has collector connected to the emitter follower connected transistor 61, serves to provide a voltage at the emitter of transistor 61 that is the inverse of the voltage presented to the base of transistor 51. The collector of transistor 61 is connected to the negative voltage source with its emitter connected via a resistor 63 to the emitter of transistor 65. The collector of transistor 65 is connected to the resistor 53 with base biased at +0.7 volts via its connection to the diode 67. Diode 67 is connected to ground at one end and to the positive voltage source via a resistor 69. The voltage provided by the diode 67, which is about +0.7 volts, serves to compensate for the 0.7 volt drop that occurs between the base and emitter junction of transistor 65. The signal present at the collector of transistor 65 is coupled by the transistor 72, that is connected as an emitter-follower, to the transistor 55, the emitter of which is connected to provide one input to the multiplier 34. A resistor 72 is connected between the emitter of transistor 71 and the negative voltage source while its collector is connected to the positive voltage source. The collector of transistor 55 is connected to the negative voltage source while its emitter is connected to the positive voltage source via a resistor 73.

With the circuit 46 of FIG. 4 as described, a signal applied to the first input (resistor 53) will cause transistor 71 to conduct and in turn cause transistor 55 to conduct so a signal that is directly related to the signal at the first input will be presented to the multiplier 34. Such description, however, disregards the compensation action that is initiated by the remainder of the circuitry. When a signal is presented to the second input (base of transistor 51), transistor 51 conducts and with a signal also present at the first input (resistor 53), transistors 65 and 61 conduct to increase the voltage drop across resistor 53, thereby decreasing the signal to transistor 71 to cause a decrease in the output to the multiplier 34 so that it is receiving a signal that, due to the signal to transistor 51, is less than that due to just the signal applied to the first input of compensation circuit 46. The output of the multiplier 34 will then be decreased, which when compared at the comparator-amplifier 36 with the reference signal from the power level selector 28, will provide a control signal to the power amplifier to cause the power delivered by the power amplifier to increase. The decrease in the output of the multiplier 34 becomes greater as the signal to the second input increases. When the signal to the first input (resistor 53) to the compensation circuit 46 is obtained from the current to voltage sensing circuit 30 with the signal to the second input (transistor 51) of circuit 46 obtained from the voltage sensing circuit 32, there will be a small increase in the power at lower end portion of the impedance range, but the compensation provided will be the most effective at the upper end portion of the impedance range. Conversely, when the signal to the first input to the circuit 46 is obtained from the voltage sensing circuit 32 with the signal to the second input of circuit 46 obtained from the current to voltage sensing circuit 30, the compensation will be the most effective at the lower end portion of the impedance range.

Obviously, many modifications and variations of the foregoing disclosure are possible in light of the above teachings. It is, therefore, to be understood that within the scope of the appended claims, the invention may be practiced otherwise than as specifically described.

What is claimed is:

1. An improved electrosurgical unit for providing electrosurgical currents to electrically conductive tissue from a controllable power amplifier connected to the primary winding of an output transformer with the secondary winding of the transformer connected to an active electrode and return electrode between which the tissue to receive an electrosurgical current is positioned, the improvement therein being a feedback control circuit comprising:

a first sensing means connected for sensing a current in the unit and providing a first signal in response thereto that is directly related to the current delivered to tissue when presented between the active electrode and return electrode;

a second sensing means connected for sensing a voltage in the unit and providing a second signal in response thereto that is directly related to the voltage presented across the tissue when presented between the active electrode and return electrode;

a multiplier circuit means for receiving two signals and providing a signal that is directly related to the mathematical product of said two signals;

a compensation circuit means having a first and a second input and responsive to signals applied to said first and second inputs for providing one of said two signals for said multiplier circuit means that is a modification of the signal applied to said first input, said modification being a function of the signal applied to said second input, said compensation circuit means connected to said multiplier circuit means to provide said one of said two signals to said multiplier circuit means, said multiplier circuit means connected for receiving one of said first and second signals as the other of said two signals, said compensation circuit means connected to said first and second sensing means for receiving said one of said first and second signals at said second input and the other of said first and second signals at said first input;

a power level selector means for providing a reference signal; and a comparator-amplifier circuit means connected for receiving said signal provided by said multiplier circuit means and connected for receiving said reference signal and having an output connected to said controllable power amplifier, said comparator-amplifier circuit means providing a signal at said output in response to said signal provided by said multiplier circuit means and said reference signal for controlling the controllable power amplifier wherein a transfer of power at a substantially constant level is made to tissue when presented between the active electrode and return electrode.

2. An improved electrosurgical unit according to claim 1 wherein said one of said first and second signals is said first signal.

3. An improved electrosurgical unit according to claim 1 wherein said one of said first and second signals is said second signal.

4. An improved electrosurgical unit according to claim 1 wherein said first sensing means is connected to the controllable power amplifier.

5. An improved electrosurgical unit according to claim 1 wherein said second sensing means is connected across the primary winding of the output transformer.

6. An improved electrosurgical unit according to claim 1 wherein said first sensing means is connected to the controllable power amplifier and said second sensing means is connected across the primary winding of the output transformer.

* * * * *